(12) United States Patent
Lanin et al.

(10) Patent No.: US 9,216,255 B2
(45) Date of Patent: Dec. 22, 2015

(54) NEEDLE ASSEMBLY

(75) Inventors: Ursula Lanin, Frankfurt am Main (DE); Bernhard Forys, Frankfurt am Main (DE); Alastair Clarke, Cheshire (GB); Matthew Ekman, Cheshire (GB); Kirsten Goode, Cheshire (GB); Michael Heald, Cheshire (GB); John Hiles, Cheshire (GB); Chris Smith, Cheshire (GB); Andrew Martin, Bristol (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 818 days.

(21) Appl. No.: 13/148,836

(22) PCT Filed: Mar. 4, 2010

(86) PCT No.: PCT/EP2010/052784
§ 371 (c)(1),
(2), (4) Date: Jan. 25, 2012

(87) PCT Pub. No.: WO2010/100240
PCT Pub. Date: Sep. 10, 2010

(65) Prior Publication Data
US 2012/0123351 A1 May 17, 2012

(30) Foreign Application Priority Data
Mar. 5, 2009 (EP) .................................... 09003181

(51) Int. Cl.
*A61M 5/00* (2006.01)
*A61M 5/32* (2006.01)

(52) U.S. Cl.
CPC ....... *A61M 5/322* (2013.01); *A61M 2005/3231* (2013.01); *A61M 2005/3235* (2013.01)

(58) Field of Classification Search
CPC ............ A61M 2005/3231; A61M 2005/3235; A61M 5/322; A61M 2005/3261; A61M 2005/5073
USPC ......................................................... 604/110
See application file for complete search history.

(56) References Cited

U.S. PATENT DOCUMENTS

| | | | |
|---|---|---|---|
| 5,049,133 A * | 9/1991 | Villen Pascual | 604/110 |
| 5,180,370 A * | 1/1993 | Gillespie | 604/110 |
| 2005/0096604 A1* | 5/2005 | Maggioni | 604/240 |

FOREIGN PATENT DOCUMENTS

| | | |
|---|---|---|
| EP | 0321903 A2 | 6/1989 |
| EP | 0677298 A1 | 10/1995 |
| EP | 1547634 A1 | 6/2005 |
| FR | 2718358 A1 | 10/1995 |
| WO | 9317735 A1 | 9/1993 |

(Continued)

OTHER PUBLICATIONS

Form PCT/IB/326, Notification Concerning Transmittal of International Preliminary Report on Patentability.

*Primary Examiner* — Emily Schmidt
(74) *Attorney, Agent, or Firm* — McDonnell Boehnen Hulbert & Berghoff LLP

(57) ABSTRACT

A needle assembly (2) for a drug delivery device (1) comprises a needle seal (3), a needle retainer (4) and a needle (5). The needle retainer (4) secures the needle (5) against displacement with respect to said needle retainer (4) when a dose of drug is being delivered. The needle seal (3) is configured to push onto the needle retainer (4) after delivering the dose of the drug, thereby unlocking the needle (5) from the needle retainer (4).

13 Claims, 2 Drawing Sheets

(56) References Cited

FOREIGN PATENT DOCUMENTS

Figure 1:
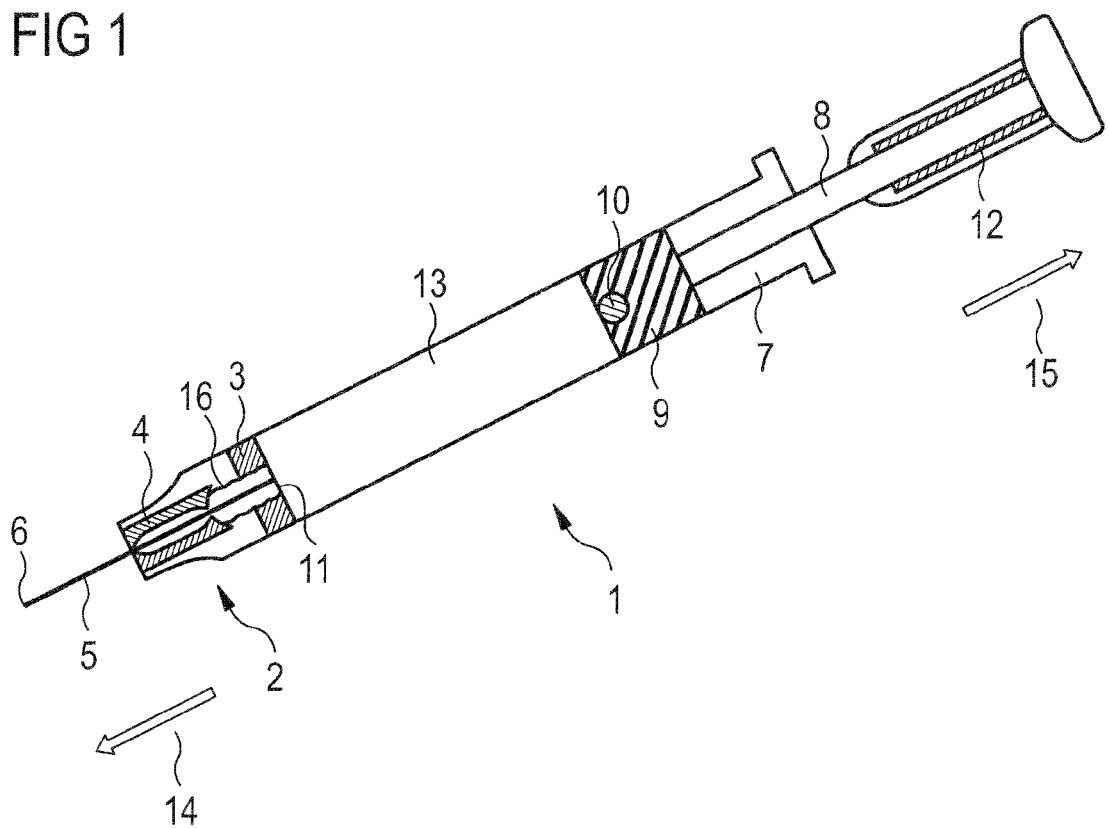

| WO | 2006108243 | A2 | 10/2006 |
| WO | 2006119270 | A1 | 11/2006 |
| WO | 2009003234 | A1 | 1/2009 |

* cited by examiner

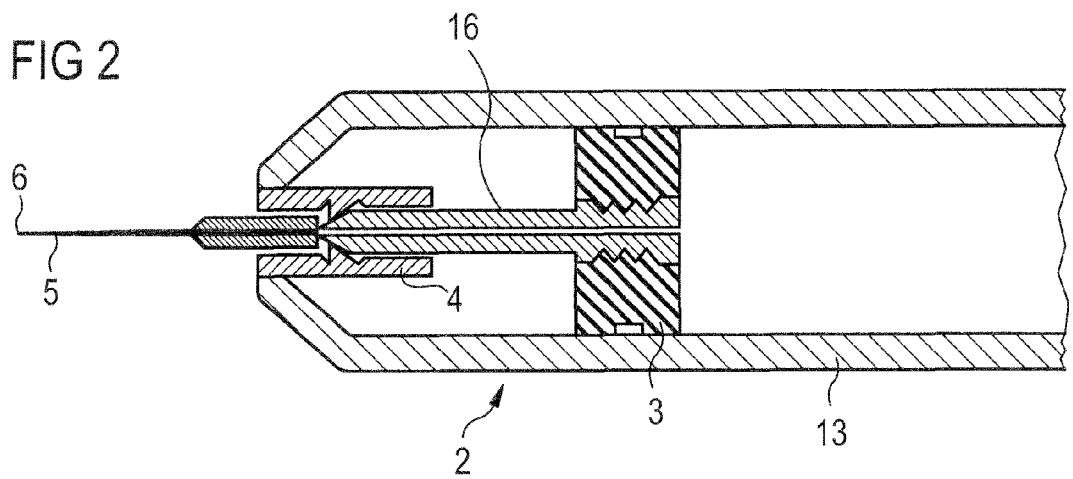
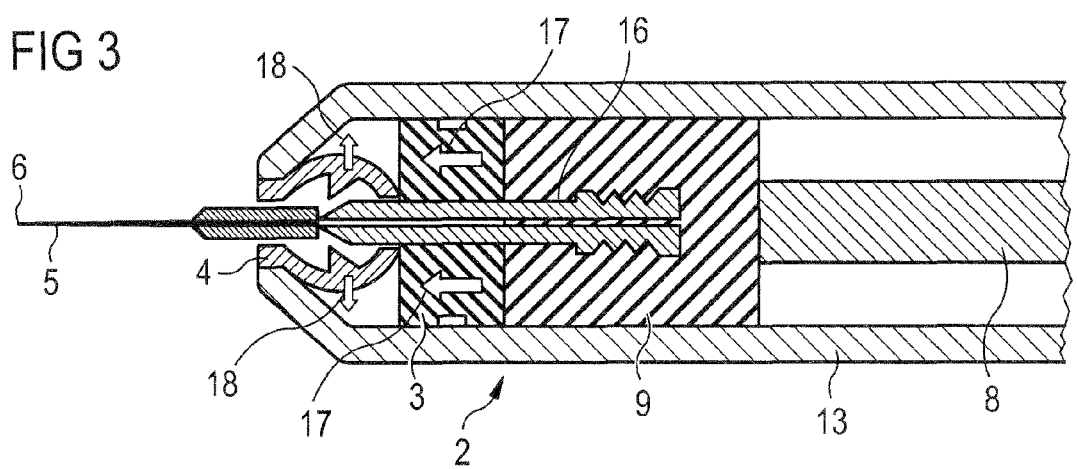
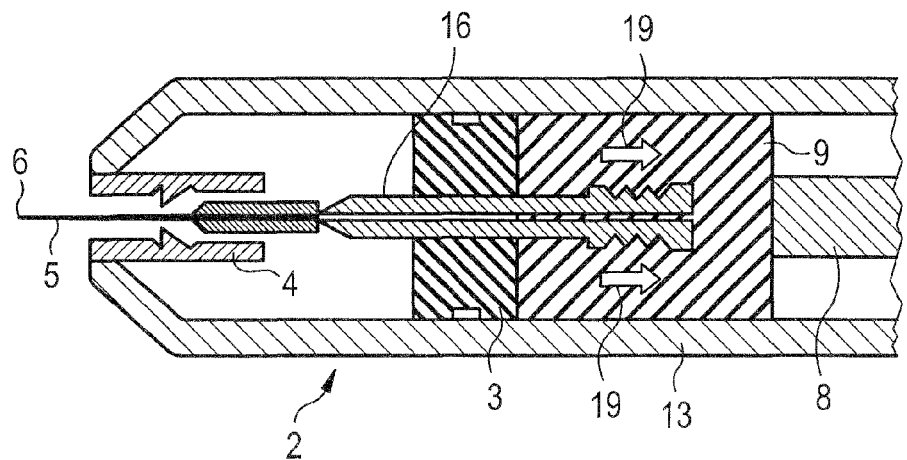

NEEDLE ASSEMBLY

CROSS REFERENCE TO RELATED APPLICATIONS

The present application is a 35 U.S.C. 371 National Application of PCT/EP2010/052784 filed Mar. 4, 2010, which claims priority to European Patent Application No. 09003181.6, filed Mar. 5, 2009, the entire contents of which are incorporated entirely herein by reference.

This disclosure relates to a needle assembly for a drug delivery device comprising a needle seal, a needle retainer and a needle.

It is of special interest to prevent re-use of injection devices, thus preventing accidental needlestick injuries and the sharing of the injection devices without adequate sterilisation, which might lead to the transfer of diverse diseases, among them Human Immunodeficiency (HIV). In addition, most injection devices bear the risk of inadvertent needlestick injuries. To prevent needlestick injuries, disposable drug delivery devices are developed wherein the needle can be retracted into the device after injection, therefore preventing the device from delivering another dose of drug and preventing accidental needlestick injuries.

Document WO 2009/003234 A1 shows a syringe with a needle retaining system comprising a retractable needle, a needle seal, a retaining member and an ejector member, which is operable to release the retractable needle from the retaining member. The syringe furthermore comprises a plunger seal capable of engaging with the retractable needle.

Document WO 2006/119570 A1 shows a syringe comprising a plunger and a needle, which is mounted to a retractable needle mount. The needle mount is held in a housing of the syringe by a releasable holding means preventing inadvertent retraction of the needle mount. The holding means comprise different holding clips as well as a serrated rim for restraint of the needle mount in the housing before retraction of the needle mount into the syringe. The needle mount can be engaged with the plunger which retracts the needle mount and hence the needle, which is mounted to the needle mount, into the syringe.

Document WO 2006/119570 A1 shows controlling means suitable for facilitating control of the rate of retraction of the needle mount and does not refer to a simple and effective unlocking of the needle mount for withdrawing the needle mount, and consequently the needle, into the syringe.

It is an object of the present invention to provide a needle assembly for a drug delivery device, comprising a needle, a needle retainer and a needle seal, which allows to unlock the needle from the needle retainer in an efficient and easy manner, thus allowing the retraction of the needle into the drug delivery device, efficiently preventing the re-use of the device as well as needlestick injuries.

This object might be achieved by a needle assembly according to the independent claim. Further features are subject matters of the dependent claims.

According to one aspect of the invention a needle assembly for a drug delivery device is provided comprising a needle seal, a needle retainer and a needle. The needle retainer secures the needle against displacement with respect to the needle retainer when a dose of a drug is being delivered. The needle seal is configured to compress the needle retainer after delivering the dose of the drug, thereby unlocking the needle from the needle retainer.

The drug delivery device is suitable to deliver a drug, in one embodiment the drug is expelled through a needle. Drug delivery devices may be designed as a pen-type injection device, auto-injector or syringe, for example a disposable pre-filled syringe.

The needle retainer is designed for fixing the needle in a predetermined position with respect to the needle retainer before and during delivery of the dose of drug. The retainer is fixed in position with respect to a housing of the injection device.

After the dose of drug has been delivered, the needle seal moves towards the needle retainer and thereby mechanically interacts directly with the needle retainer so that the needle retainer releases the needle. No further ejecting means for releasing the needle from the needle retainer are necessary.

According to a preferred embodiment, the needle seal is configured to deform the needle retainer after delivering the dose of the drug.

When the needle seal pushes onto the needle retainer after the dose of the drug has been delivered, the needle seal transfers mechanical force to the needle retainer. Thus, the needle retainer is compressed, gets deformed (i.e. changes its shape) and therefore unlocks the needle which is then free to move with respect to the needle retainer and with respect to the housing of the drug delivery device.

According to another preferred embodiment, the needle retainer is configured to bow radially outwards with respect to the needle when the needle seal is deforming the needle retainer.

When the needle seal imparts pressure to the needle retainer the needle retainer preferably bends outwards or buckles. Consequently, the needle is unlocked, and the dispensing end of the needle can be moved proximally. In a next step the needle can be retracted into the drug delivery device.

In a preferred embodiment unlocking the needle from the needle retainer allows movement of a dispensing end of the needle in a proximal direction with respect to the needle retainer. Hence, the needle is movable with respect to the needle retainer and can therefore be retracted into the drug delivery device. Consequently, a re-use of the drug delivery device as well as needlestick injuries are prevented.

In a preferred embodiment, the needle retainer is made of a flexible material. On the one hand this allows a very easy and flexible securing of the needle in the needle retainer which is independent from the type and, especially, the size of the used needle. On the other hand this embodiment makes it possible that the needle retainer can change its shape when pushed on by the needle seal, permitting a quick and effective release of the needle.

The flexible material of the needle retainer might be rubber, plastic or any other material which can change its shape when mechanical force is transferred to it.

In another preferred embodiment, the needle retainer is made of a rigid material. This embodiment guarantees a cheap and easy realisation of the invention, as also standard needle retainers might be used for this embodiment of the present invention.

In a further preferred embodiment the needle seal is configured to break the needle retainer when pushing onto said needle retainer.

Preferably, the needle retainer is made of a rigid material, which might be a rigid plastic or any other rigid material which breaks when mechanical force is transferred to it in the appropriate direction. When the needle seal exerts pressure on the needle retainer the rigid material of the needle retainer cracks and is preferably destroyed completely, which means that the needle retainer cannot be used anymore for securing the needle against displacement with respect to the needle retainer, the needle is unlocked from the needle retainer.

Therefore, it is possible to retract the needle into the drug delivery device and hence, a re-use of the corresponding drug delivery device can be excluded in a very effective manner.

The object of the present invention might also be achieved by a drug delivery device comprising the before-mentioned needle assembly.

According to one aspect a drug delivery device is provided which comprises the needle assembly as well as a plunger assembly and a housing. The plunger assembly is configured to move in a distal direction with respect to the housing, thereby pushing the needle seal of the needle assembly in the distal direction of the drug delivery device.

The plunger assembly may contain a plunger, which can be depressed by a user, i.e. be moved in the distal direction with respect to the housing, for delivering the dose of the drug. Furthermore, the plunger assembly may comprise a plunger seal, providing a fluid seal, which means that the drug cannot move between the housing and the plunger assembly.

The needle assembly and the plunger assembly are fixed to the housing. The housing may comprise a barrel, which is preferably built from glass or plastic. The barrel may serve as a protective cover of a cartridge holder comprising a cartridge, which contains the dose of the drug. The cartridge holder is fixed to the housing in that way that the cartridge holder is preferably glued to the barrel.

A dose of the drug is delivered when the plunger assembly moves to distal direction with respect to the housing. The movement of the plunger assembly allows abutment of the plunger seal and the needle seal when the dose has been delivered completely. In a further step—when further depressing the plunger assembly after the dose of drug has been delivered—the needle seal is moved by the plunger assembly towards the needle retainer and finally comes into contact with the needle retainer, exerting pressure on the needle retainer pushing onto it, which further serves to unlock the needle, which can then be retracted into the drug delivery device preventing re-use as well as needlestick injuries and guaranteeing safe disposal of the device.

According to a preferred embodiment the plunger assembly comprises engaging means for engaging the needle of the needle assembly after delivering the dose of the drug. This allows an easy retraction of the needle into the drug delivery device together with a retraction of the plunger assembly.

Preferably, one embodiment of the engaging means comprises a nib or a notch or engaging clips or any other means being suitable for engaging with the needle.

According to a preferred embodiment, the needle assembly comprises mating means which engage with the engaging means of the plunger assembly after delivering the dose of the drug.

Preferably, the engaging means comprise a nib or a notch or engaging clips or any other means being suitable for engaging with the engaging means of the plunger assembly.

According to a preferred embodiment of the invention, the plunger assembly and the needle are configured to be withdrawn manually into the housing of the drug delivery device when a proximal force is imparted to the plunger assembly.

Preferably, a user keeps on depressing the plunger assembly after the dose has been delivered. Thereby, the plunger assembly engages with the needle and is finally forced back into the housing.

According to a preferred embodiment, the drug delivery device further comprises retraction means, wherein the retraction means are configured to automatically withdraw the plunger assembly and the needle into the housing of the drug delivery device.

Preferably, the retraction means may comprise a spring or a clip. The retraction means may be decompressed after the plunger assembly has engaged with the needle, automatically drawing the plunger assembly and the needle into the housing of the drug delivery device.

According to another preferred embodiment the drug delivery device is a syringe pre-filled with a medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features and refinements become apparent from the following description of the exemplary embodiments in connection with the accompanying figures.

FIG. 1 schematically shows a drug delivery device comprising a needle assembly according to the present invention, FIG. 2 schematically shows a more detailed view of a part of the drug delivery device of FIG. 1 before delivering the dose of the drug, FIG. 3 schematically shows the part of the drug delivery device of FIG. 2 after the dose of the drug has been delivered, FIG. 4 schematically shows the part of the drug delivery device of FIG. 2 and FIG. 3 during retraction of a needle.

Turning to FIG. 1, a drug delivery device 1 is presented comprising a distal end and a proximal end. The distal end is indicated by the solid arrow 14 on the left hand side, which refers to that end of the drug delivery device 1 which is closest to the dispensing end of the drug delivery device 1. The drug delivery device 1 further comprises a proximal end, indicated by the solid arrow 15 on the right hand side, referring to the end which is opposite to the dispensing end of the device 1.

The drug delivery device 1 further comprises a housing 13 and a needle assembly 2. The housing 13 may be shaped as a barrel and is configured to contain the drug. The needle assembly 2, which is located at the distal end of the housing 13, comprises a needle seal 3, a needle retainer 4 and a needle 5. The needle 5 has a dispensing end 6 and comprises a needle mount 16 formed as a coating on the proximal end of the needle 5, or as formed features on the needle 5.

The drug delivery device 1 further comprises a plunger assembly 7, comprising a plunger 8 and a plunger seal 9. The plunger 8 is moveable in the distal direction with respect to the housing 13 so that the plunger seal 9 moves along the housing 13. The plunger seal 9 contains engaging means 10. Furthermore, the needle assembly 2 comprises mating means 11. The drug delivery device 1 has retraction means 12 suitable to retract the needle 5 when the drug is delivered.

In this embodiment the drug delivery device 1 is designed as a disposable pre-filled safety syringe having a retractable needle.

The drug delivery device 1 comprises the housing 13. If the drug delivery device 1 is a syringe, as shown in FIG. 1, the housing 13 is shaped as a barrel.

If the drug delivery device 1 is a pen-type injection device (not shown in FIG. 1), the housing 13 might contain further elements, for example a cartridge holder (not shown in FIG. 1) containing a cartridge, wherein the dose of drug is stored.

The barrel may be built from glass, metal or plastic. The plunger 8 and the plunger seal 9 can move within the barrel.

The needle assembly 2 comprises the needle seal 3, the needle retainer 4 and the needle 5. The needle seal 3 might be made of a resilient material, for example rubber or plastic, and provides a fluid seal between the housing 13 and the needle assembly 2. The needle seal 3 is releasably secured against displacement with respect to the housing 13 during delivery of the dose of the drug. The needle seal 3 is intended to move in the distal direction with respect to the housing 13 only after having delivered the dose of drug when being pushed on it. The needle seal 3 might be releasably engaged with the housing 13 of the drug delivery device 1, for example by means of engaging clips or a flange or by mechanical friction.

The needle retainer 4 is locked in its position with respect to the housing 13, for example by engaging clips or a flange, which may be arranged circumferentially within the housing 13 of the drug delivery device 1. The needle retainer 4 might also be glued to the housing 13. The needle retainer 4 secures the needle 5 against displacement with respect to the needle retainer 4 while delivering the dose of drug.

The needle is covered with a plastic layer (i.e. needle mount 16), which increases the friction and facilitates engaging of the mating means 11 of the needle assembly 2 with the engaging means 10 of the plunger seal 9 as described later on in more detail.

The needle 5 is preferably secured within the needle retainer 4 by means of mechanical friction. The needle retainer 4 might be made of a flexible or a rigid material.

In this embodiment the plunger assembly 7 contains the plunger 8 and the plunger seal 9, which is preferably made of resilient material providing a fluid seal in proximal direction with respect to the housing 13. The plunger seal 9 may be integrally formed with the plunger 8. However, the plunger seal 9 and the plunger 8 can also be separately formed, i.e. the plunger seal 9 could be connected to the plunger 8. The plunger seal 9 can be held at its position within the housing 13 by means of mechanical friction.

When the dose of drug is to be delivered the user depresses the plunger 8, which then moves in distal direction with respect to the housing 13. Thereby, the plunger seal 9 is also pushed in distal direction with respect to the housing 13, hence moving towards the needle assembly 2, abutting the needle seal 3 after the content has been dispensed.

The plunger seal 9 exerts pressure on the needle seal 3, releasing it from its position within the housing 13. The plunger seal 9 then forces the needle seal 3 in distal direction with respect to the housing 13 and thus, the needle seal 3 moves the needle mount 16 down towards the needle retainer 4. Thereby, the needle seal 3 releases the proximal end of the needle 5 which was previously covered by the needle seal 3. This enables a connecting of the proximal end of the needle, i.e. of the mating means 11 of the needle assembly 2 which are located at the proximal end of the needle 5, with the engaging means 10 of the plunger seal 9.

For this purpose, plunger seal 9 comprises the engaging means 10 which are suitable to engage with the mating means 11 of the needle assembly 2, i.e. the proximal end of the needle 5. Thereby, the engaging means 10 might comprise a lug and the mating means 11 might comprise a notch or vice versa.

In this embodiment the engaging means 10 comprise a notch. When the proximal end of the needle 5 is no longer covered by the needle seal 3, i.e. the needle seal 3 is pushed in distal direction by the plunger seal 9, the notch deforms to the mating means 11 (formed as a cavity within the needle seal 3) of the needle assembly 2, i.e. the proximal end of the needle 5, which is covered with the plastic layer, i.e. the needle mount 16, and engages with said proximal end of the needle 5 by means of mechanical friction.

By being pushed further in the distal direction with respect to the housing 13, the needle seal 3 is pushed towards the needle retainer 4 so that force is transferred to the needle retainer 4.

If the needle retainer 4 is made of a flexible material, for example rubber, the needle retainer 4 might consequently be deformed by the needle seal 3. Thus, the needle retainer 4 may buckle or bow radially outwards with respect to the needle 5. Thereby, the degree of buckling or bowing outwards has to be sufficient to unlock the needle 5 from its position within the needle retainer 4. Once the needle 5 is unlocked from the needle retainer 4 the dispensing end 6 of the needle 5 can move towards the needle retainer 4. The degree of buckling or bowing outwards must be sufficient to ensure that reengagement cannot occur during withdrawal of the needle 5, i.e. the buckled/bowed needle retainer 4 must not reengage with the needle 5.

If the needle retainer 4 is made of a flexible material the needle retainer 4 may spring back into its original shape after the needle 5 has been retracted into the drug delivery device 1 and after the needle seal 3 has stopped pushing onto the needle retainer 4.

If the needle retainer 4 is made of a rigid material the needle seal 3 might break the needle retainer 4 when pushing onto it, i.e. breaking arms of the needle retainer 4, thus also releasing the needle 5 from its position within the needle retainer 4.

After the needle 5 has been unlocked it can be retracted into the housing 13 of the drug delivery device 1 for a safe disposal of the device 1. For this purpose, one embodiment of the drug delivery device 1 comprises retraction means 12, which might be designed as a spring or other energy storage device. After disengaging the needle 5 from the needle retainer 4 the retraction means 12 might automatically push the plunger assembly 7 (in this embodiment the plunger 8 and the plunger seal 9) and therefore the needle 5, which is engaged with the plunger seal 9, backwards into the housing 13.

For this purpose, the compressed retraction means 12 must decompress. Thereby, movement of the plunger 8 in distal direction with respect to the housing 13 might bring an engaging arm to bear against a release ring (not shown in FIG. 1) at the proximal end of the housing 13. Said release ring may be mounted or otherwise fitted to the housing 13. Said release ring may move the engaging arm transversally with respect to the housing 13 and out of engagement with a rim (not shown in FIG. 1) of the plunger assembly 7. This disengagement allows the compressed retraction means 12 to decompress and to push against a ledge (not shown in FIG. 1) of the plunger 8, thereby retracting the plunger assembly 7 and the needle 5 coupled thereto. Hence, a re-use of the drug delivery device 1 is prevented and a safe disposal of the device 1 is guaranteed.

However, the retraction of the plunger assembly 7 and the needle 5 into the housing 13 might also be manually driven by a user, who keeps on depressing the plunger 8 after the dose has been delivered until after releasing the needle 5 from the needle retainer 4, then manually retracting the plunger 8 and needle 5.

FIG. 2 schematically shows a more detailed view of a part of the drug delivery device 1 of FIG. 1 before delivering the dose of drug. The same reference numerals apply for the description of FIG. 2 as for the description of FIG. 1.

FIG. 2 represents a more detailed view of the distal end of the drug delivery device 1 containing the needle assembly 2. The needle assembly 2 comprises the needle seal 3, the needle retainer 4 and the needle 5 with the dispensing end 6. The needle is covered by a plastic coating forming the needle mount 16. Furthermore, the drug delivery device 1 comprises the housing 13.

FIG. 2 shows the drug delivery device 1 before delivering the dose of drug. Hence, the needle 5 is secured to the needle retainer 4 against displacement with respect to the needle retainer 4. Thereby, the needle 5 and the needle retainer 4 fit together optimally, the needle retainer 4 comprising, for example, protrusions keeping the needle 5 secured to the needle retainer 4. However, the needle 5 can also be secured to the needle retainer 4 by means of mechanical friction, the mechanical friction being increased by means of the needle mount 16, i.e. the plastic coating the needle 5 is covered with.

The needle retainer 4 may be made of a rigid or a flexible material. In this embodiment the needle retainer 4 is made of a flexible material. As far as the engagement of the needle retainer 4 within the housing 13 is concerned, the same methods of realisation can be applied as already mentioned during the description of FIG. 1. The needle retainer 4 stays in its original state until the dose of drug has been delivered.

The needle seal 3 is positioned at the proximal end of the needle 5. During delivery of the dose the needle seal 3 is (releasably) engaged with the housing 13, for example by means of mechanical friction or a flange. After the dose has been delivered completely the needle seal 3 is pushed by the plunger seal 9 in distal direction with respect to the housing 13.

When the needle 5 and the plunger assembly 7 are retracted into the housing, as described previously, the needle seal 3 may or may not be drawn—together with the plunger assembly 7 and the needle 5—in proximal direction with respect to the housing 13 (see FIG. 4).

FIG. 3 schematically shows the part of the drug delivery device 1 of FIG. 2 after the dose of the drug has been delivered. FIG. 3 further shows the plunger 8 and the plunger seal 9.

For delivering the dose of drug the user depresses the plunger 8, which then moves together with the plunger seal 9 in distal direction with respect to the housing 13. After the dose has been delivered the plunger seal 9 abuts the needle seal 3 and forces it into distal direction with respect to housing 13, as indicated by the large solid arrows 17 pointing to the left.

The needle seal 3 moves towards the needle retainer 4, comes into contact with it and thereby the needle seal 3 exerts pressure on the needle retainer 4, which is made of a flexible material in this embodiment, for example plastic or stainless steel. Under the exerted pressure the flexible needle seal 4 is deformed and bows radially outwards with respect to the needle 5, as indicated by the small solid arrows 18. As the needle retainer 4 is bowed outwards the needle 5 is unlocked from the needle retainer 4, allowing movement of the distal end 6 of the needle 5 in proximal direction with respect to the needle retainer 4 and hence the complete retraction of the needle 5 into the drug delivery device 1. The degree of bowing outwards must be sufficient to ensure that the needle is completely unlocked from the needle retainer 4 and that the needle 5 is not reengaged when withdrawing the needle 5 into the drug delivery device 1. Hence, the needle retainer 4 must not engage with the needle 5 anymore when said needle retainer 4 is bowed radially outwards.

For an easy retraction of the needle 5 the plunger seal 9 and the needle assembly 2 comprise engaging means 10 and mating means 11, which engage with each other after the dose of drug has been delivered. For retracting the needle 5, the plunger 8 and the plunger seal 9, the drug delivery device 1 might comprise the retraction means 12, for example a spring, as was already explained when describing FIG. 1.

FIG. 4 schematically shows the part of the drug delivery device of FIG. 2 and FIG. 3 during retraction of a needle 5.

After unlocking the needle 5 from the needle retainer 4 (FIG. 3) the needle 5 can be retracted into the drug delivery device 1 (see solid arrow 19) as was explained when describing FIG. 1. The retraction is facilitated by means of the engaging means 10 and mating means 11 of the plunger seal 9 and the needle assembly 2 which engage when the plunger seal 9 abuts the needle seal 3 forcing it into distal direction with respect to the housing 13 after the dose of drug has been delivered.

When retracting the plunger assembly 7 and the needle 5 into the drug delivery device 1 the needle seal 3 might also be drawn in proximal direction with respect to the housing 13, as indicated in FIG. 4.

Other implementations are within the scope of the following claims. Elements of different implementations may be combined to form implementations not specifically described herein.

The invention claimed is:

1. A needle assembly for a drug delivery device, wherein the needle assembly comprises
   a needle seal,
   a needle retainer and a needle, wherein
   the needle retainer secures the needle against displacement with respect to said needle retainer when a dose of a drug is being delivered, wherein the needle retainer is in an original state until the dose is delivered,
   the needle retainer is made of a flexible material, and
   said needle seal is configured to push onto, compress, and deform the needle retainer after delivering the dose of the drug, thereby unlocking the needle from the needle retainer, wherein
   the needle retainer is configured to bow radially outwards with respect to the needle when the needle seal is deforming the needle retainer, and
   the needle retainer is configured to spring back into the original state after the needle is retracted into the drug delivery device.

2. The needle assembly according to claim 1, wherein unlocking the needle from the needle retainer allows movement of a dispensing end of the needle in a proximal direction with respect to the needle retainer.

3. A drug delivery device comprising the needle assembly according to claim 1, further comprising a plunger assembly and a housing, wherein the plunger assembly is configured to move in a distal direction with respect to the housing, thereby pushing the needle seal of the needle assembly in the distal direction of the drug delivery device.

4. The drug delivery device according to claim 3, wherein the plunger assembly comprises engaging means for engaging the needle of the needle assembly after delivering the dose of the drug.

5. The drug delivery device according to claim 4, wherein the needle assembly comprises mating means which engage with the engaging means of the plunger assembly after delivering the dose of the drug.

6. The drug delivery device according to claim 3, wherein the plunger assembly and the needle are configured to be withdrawn manually into the housing of the drug delivery device when a proximal force impacts to the plunger assembly.

7. The drug delivery device according to claim 3, wherein the drug delivery device further comprises retraction means, which are configured to automatically withdraw the plunger assembly and the needle into the housing of the drug delivery device.

8. The drug delivery device according to claim 7, wherein the retraction means comprise a spring.

9. The drug delivery device according to claim 3, wherein the drug delivery device is a pen-type injection device.

10. The drug delivery device according to claim 3, wherein the drug delivery device is a syringe pre-filled with a medicament.

11. A needle assembly for a drug delivery device, wherein the needle assembly comprises
a needle seal,
a needle retainer and a needle, wherein
the needle retainer secures the needle against displacement with respect to said needle retainer when a dose of a drug is being delivered, wherein the needle retainer is in an original state until the dose is delivered,
the needle retainer is made of a flexible material, and
said needle seal is configured to push onto, compress, and deform the needle retainer after delivering the dose of the drug, thereby unlocking the needle from the needle retainer, wherein
the needle retainer is configured to bow radially outwards with respect to the needle when the needle seal is deforming the needle retainer,
the needle retainer is configured to spring back into the original state after the needle is retracted into the drug delivery device,
wherein the needle seal is movable with respect to the needle,
a plunger seal,
the needle seal arranged between the needle retainer and the plunger seal,
the plunger seal is movable with respect to the needle and the needle seal, and
the plunger seal is provided for exerting pressure on the needle seal towards the needle retainer.

12. The needle assembly according to claim 11, wherein unlocking the needle from the needle retainer allows movement of a dispensing end of the needle in a proximal direction with respect to the needle retainer.

13. A drug delivery device comprising the needle assembly according to claim 11, further comprising
a plunger assembly and a housing, wherein the plunger assembly is configured to move in a distal direction with respect to the housing, thereby pushing the needle seal of the needle assembly in the distal direction of the drug delivery device,
wherein the plunger assembly comprises the plunger seal.

* * * * *